United States Patent
Alster et al.

(10) Patent No.: US 6,656,131 B2
(45) Date of Patent: Dec. 2, 2003

(54) METHOD AND SYSTEM FOR DETECTING EYE DISEASE

(75) Inventors: Yair Alster, Tel-Aviv (IL); Omer Rafaeli, Givatayim (IL); Barak Azmon, Tel-Aviv (IL)

(73) Assignee: Notal Vision Inc., New Castle, DE (US)

( * ) Notice: Subject to any disclaimer, the term of this patent is extended or adjusted under 35 U.S.C. 154(b) by 0 days.

(21) Appl. No.: 09/781,548

(22) Filed: Feb. 13, 2001

(65) Prior Publication Data

US 2002/0042580 A1 Apr. 11, 2002

(30) Foreign Application Priority Data

Oct. 6, 2000 (IL) .................................. 138926

(51) Int. Cl.[7] .............................................. A61B 13/00

(52) U.S. Cl. ...................................... 600/558

(58) Field of Search ............................... 600/558, 300, 600/301; 351/200–221, 246; 705/1–4

(56) References Cited

U.S. PATENT DOCUMENTS

| | | | |
|---|---|---|---|
| 4,798,456 A | | 1/1989 | Enoch et al. |
| 4,822,162 A | | 4/1989 | Richardson et al. |
| 4,995,717 A | * | 2/1991 | Damato ...................... 351/224 |
| 5,589,897 A | * | 12/1996 | Sinclair et al. ............. 351/223 |
| 5,864,384 A | | 1/1999 | McClure et al. |
| 5,892,570 A | | 4/1999 | Stevens |
| 5,946,075 A | * | 8/1999 | Horn ........................... 351/246 |
| 6,027,217 A | | 2/2000 | McClure et al. |
| 6,033,076 A | | 3/2000 | Braeuning et al. |

OTHER PUBLICATIONS

Jay M. Enoch et al., "Hyperacuity Perrimetry: Assessment of Macular Function Through Ocular Opacities", Arch Opthalmol, vol. 112, Aug. 1984, pp. 1164–1168.

Michael Wall and Alfredo A. Sadun, "Threshold Amsler Grid Testing: Cross–Polarizing Lenses Enhance Yield", Arch Ophthalmol, vol. 104, Apr. 1986, pp. 520–523.

Stuart L. Fina and The Macular Photocoagulation Study Group, "Early Detection of Extrafoveal Neovascular Membranes by Daily Central Field Evaluation", Wilmer Opthalmological Institute, John Hopkins University, John Hopkins University, presented at meeting which took place betwen Oct. 30–Nov. 3, 1984, pp. 603–609.

Vasudevan Lakshminarayanan et al., "Quantifications of Metamorphopsia Using Hyperacuity Techniques", Optometry and Vision Science, vol. 68, No. 12,, 1991, pp. 942–945.

Michael J. Tolentino et al., "Visual Field Deficits in Early Age–Related Macular Degeneration", Vision Res., vol. 34, No. 3, pp. 409–413, 1994.

Reginald G. Ariyasu et al., "Sensitivity, Specificity and Predicitive Values of Screening Tests for Eye Conditions in a Clinic–Based Population", Ophthamology, vol. 103, No. 11, Nov. 1996, pp. 1751–1760.

* cited by examiner

*Primary Examiner*—Max F. Hindenburg
*Assistant Examiner*—Pamela Lynn Wingwood
(74) *Attorney, Agent, or Firm*—Eitan, Pearl, Latzer & Cohen Zedek, LLP (57) ABSTRACT

A method and system for detecting eye disease. A pattern is displayed on a screen to an individual, who is made to fixate his vision on a point in the pattern. The pattern is then hidden and a second pattern is displayed. The individual then compares the second pattern, as perceived by him, with a pre-defined pattern. These steps are then repeated several times. It is then determined whether the individual has an eye disease based on the comparisons.

42 Claims, 4 Drawing Sheets

METHOD AND SYSTEM FOR DETECTING EYE DISEASE

FIELD OF THE INVENTION

This invention relates to systems and methods for detecting eye disease.

BACKGROUND OF THE INVENTION

Age-related macular degeneration (AMD) is the leading cause of blindness among people over the age of 50 in the western world. It is a bilateral, although asymmetric disease, and comes in two forms:

Dry or non-neovascular AMD is the more common and milder form of AMD, accounting for 85–90% of all AMD. The key identifier for dry AMD is small, round, white-yellow lesions in the macula. Vision loss associated with dry AMD is far less dramatic than in the case of wet AMD. There is currently no treatment available for dry AMD. It is estimated that as many as 14 million people suffer from dry AMD in the United States alone.

Wet AMD is less prevalent than the dry form, accounting for about 10–15% of AMD cases. The term wet denotes choroidal neovascularization (CNV), in which abnormal blood vessels develop beneath the retinal pigment epithelium (RPE) layer of the retina. Wet AMD is characterized by the development of choroidal angiogenesis which causes severe, and potentially rapid, visual deterioration. The visual distortion typically consists of perceiving straight lines as curved due to deformation of the retina in a region overlying the choroidal angiogenesis. The wet form accounts for about 60% of all cases of adult blindness in the United States. In the US alone there are 200,000 new cases of wet AMD every year and a total of 1.7 million blind people from AMD.

Treatment modalities for wet AMD include conventional treatments such as laser photocoagulation and newer treatment modalities such as PhotoDynamic therapy (PDT). Experimental treatments that are under current investigation include feeder vessel coagulation and Trans-pupillary ThermoTherapy (TTT). All these proven or experimental therapies may halt or slow progression of the disease only if detected at an early stage and will not reverse existing retinal damage. Therefore, early detection is crucial to prevent severe visual loss.

Since approximately 12% of dry AMD cases develop wet AMD and subsequent blindness within 10 years, a patient diagnosed with dry AMD must be routinely examined by an ophthalmologist once or twice a year, depending on the severity of his condition. The patient is usually also given a so-called "Amsler grid" for weekly self-examination at home for symptoms of wet AMD. The patient is advised to consult an ophthalmologist immediately in the event that symptoms are noticed. The Amsler grid and its modifications (such as the "threshold Amsler" or the "red Amsler") have been displayed to be poor detectors of early changes associated with wet AMD for several reasons. One is the phenomenon of "filling-in" whereby the brain fills in missing parts in the pattern or corrects defects in the pattern. The subject thus fails to perceive a distorted pattern as being distorted. Another problem with the Amsler grid is the inability of patients to adequately fixate their vision on a fixed point while taking the test. The Amsler test also suffers from low compliance stemming from the non-interactive nature of the test.

The degree of visual deterioration is a function of the size of the lesion and its proximity to the fovea at the time of diagnosis. Although most lesions probably start outside the foveal area, 70% are already foveal and large (>1500 microns) at the time of diagnosis. It is therefore crucial to identify the lesions at the earliest possible stage, while they are still small and have not reached the fovea. It is known that 70% of lesions diagnosed as treatable become untreatable within less than three months, which indicates that the progression of the disease is relatively rapid. As many as 70–80% of patients with wet AMD are already ineligible for treatment when they first consult their ophthalmologist because the disease has progressed considerably. This is due to the poor validity of existing self-assessment methods for detecting an AMD-related lesion at an early stage, and the time lapsed between noticing the symptoms and seeing an ophthalmologist.

A reliable method for diagnosing wet AMD at the earliest possible stage, in conjunction with a referral system aimed at lowering the incidence of visual deterioration in this devastating disease, are imperative. If detected early, laser therapy to destroy the abnormal blood vessels may prevent additional vision loss. It is therefore crucial to detect the transition from dry to wet AMD as early as possible.

SUMMARY OF THE INVENTION

The present invention provides an eye test for detecting retinal lesions such as those associated with AMD or diabetes. The method involves showing a subject a first pattern displayed on a surface. The pattern may be, for example, one or more lines. The subject then fixates his vision on a point on the surface. The first pattern is hidden and a second pattern is displayed at a different location on the surface. The second pattern may be substantially identical to the first pattern, or the two patterns may be different. The subject is then asked to compare the second pattern and a predefined pattern. If the second pattern and the predefined pattern were identical, but the subject has perceived them to be different, this is indicative of a lesion of the retina. The subject indicates a region in the second pattern that appears to him to be different from the same region in the predefined pattern. The location of the lesion on the retina is determined from the location of the region in the second pattern on the surface relative to the point where the subject's vision was fixated. If the second pattern and the predefined pattern were not identical, but the subject reports that the two patterns were identical, this would indicate that he is not responding reliably to the test. Thus, the second pattern may be obtained by modifying the predefined pattern to simulate the predefined pattern as perceived by a person with an eye disease. For example, the second pattern may be obtained from the predefined pattern by displacing a component of the predefined pattern, removing a component of the predefined pattern, blurring a component, or altering an optical property of a component of the predefined pattern, such as color or intensity. Such modified patterns may also be used to demonstrate to subjects various types of visual disturbances associated with retinal lesions.

Since the subject will spontaneously shift his vision to the second pattern within about 200 msec after it appears, the subject may additionally or alternatively be asked to indicate whether any motion occurred of part of the second pattern relative to other parts of the second pattern as he shifted his vision, and if so, where in the second pattern the motion occurred. For example, a segment of a line that appears curved when in the periphery of the subject's field of vision may appear to straighten as the subject shifts his vision and brings the pattern into the center of his field of vision. This apparent movement at the particular location in the pattern as the subject shifts his vision is indicative of a retinal abnormality in the corresponding region of the retina.

The test is repeated several times, each time presenting the second pattern in a different region in the subject's field of view. This allows a retinal abnormality to be mapped on the retina.

In a preferred embodiment, the method is performed by displaying the patterns on a monitor screen such as a computer monitor, television, or stand-alone device. In this embodiment, the subject can be made to fixate his vision on a point of the screen by having him bring a cursor to the point on the screen using any computer input device such as a computer mouse, a keyboard, joystick or touch-screen. This causes the first pattern to disappear from the screen and for the second pattern to appear. The patterns may consist of one or more broken lines consisting of a plurality of segments. The subject indicates a segment in the second pattern that appears different to him than the corresponding segment in the first pattern by bringing the cursor to the point and clicking the mouse. For example, if the first and second patterns are broken lines, and the subject perceives the first pattern as being straight, but perceives the second pattern as having one or more unaligned segments, the subject would click the unaligned segments with the mouse.

The results of the test are typically transmitted in real time over a communications network to a processor. The network may be a computer network such as the Internet, local and wide are networks such as LAN, WAN, or PAN. The network may also be a telephone network using a modem and TCP/IP connection. The processor that analyzes the subjects responses and generates a diagnosis of the subject's condition. The diagnosis and a recommendation for follow-up or referral for prompt examination are then transmitted over the communication system to the subject and to his care provider. The subject's compliance may be monitored regularly by the processor by storing in a memory the dates that the subject is to perform the test. Failure to perform the test on schedule results in a reminder being sent to the subject over the communication network or by telephone to perform the test. A notice may also be sent to the health care provider.

Thus, in its first aspect the invention provides a method for detecting eye disease in an individual, comprising steps of:
- displaying to the individual a first pattern at a first location on a surface, the first pattern consisting of at least one point;
- fixating the individual's vision on a point in the first pattern;
- hiding at least a portion of the first pattern;
- displaying a second pattern to the individual at a second location on the surface so as to allow the individual to form a perceived image of the second pattern;
- obtaining a comparison of the perceived image and a predefined pattern;
- repeating the first step of displaying, the step of fixating, the step of hiding, the second step of displaying, and the step of obtaining a number of times; and
- determining whether the individual has an eye disease based on the comparisons.

In its second aspect, the invention provides a system for detecting eye disease in an individual, comprising;
- (a) a surface configured to display a first pattern to the individual, the pattern consisting of at least one point;
- (b) a device for fixating the individual's vision on a point in a pattern displayed on the surface and hiding the pattern after the individual's vision has been fixated on the point; and
- (c) a device for selecting a portion of a pattern displayed on the surface.

In its third aspect, the invention provides a program storage device readable by machine, tangibly embodying a program of instructions executable by the machine to perform method steps for detecting eye disease in an individual, comprising steps of:
- displaying to the individual a first pattern at a first location on a surface, the first pattern consisting of at least one point;
- determining when the individual's vision is fixated on a point in the pattern;
- hiding at least a portion of the first pattern upon the individual fixating his vision on a point in the first pattern;
- displaying a second pattern to the individual at a second location on the surface so as to allow the individual to form a perceived image; and
- obtaining a comparison of the perceived image and a predefined pattern;

In its fourth aspect, the invention provides a computer program product comprising a computer useable medium having computer readable program code embodied therein for detecting eye disease in an individual, the computer program product comprising:
- computer readable program code for causing the computer to display a first pattern to the individual at a first location on a surface;
- computer readable program code for causing the computer to determine when the individual's vision is fixated on a point on the surface and for hiding at least a portion of the first pattern when the individual's vision is fixated on the point;
- computer readable program code for causing the computer to display a second pattern to the individual at a second location on the surface so as to allow the individual to form a perceived image of the second pattern and;
- computer readable program code for causing the computer to obtain a comparison of the perceived image and the predefined pattern.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
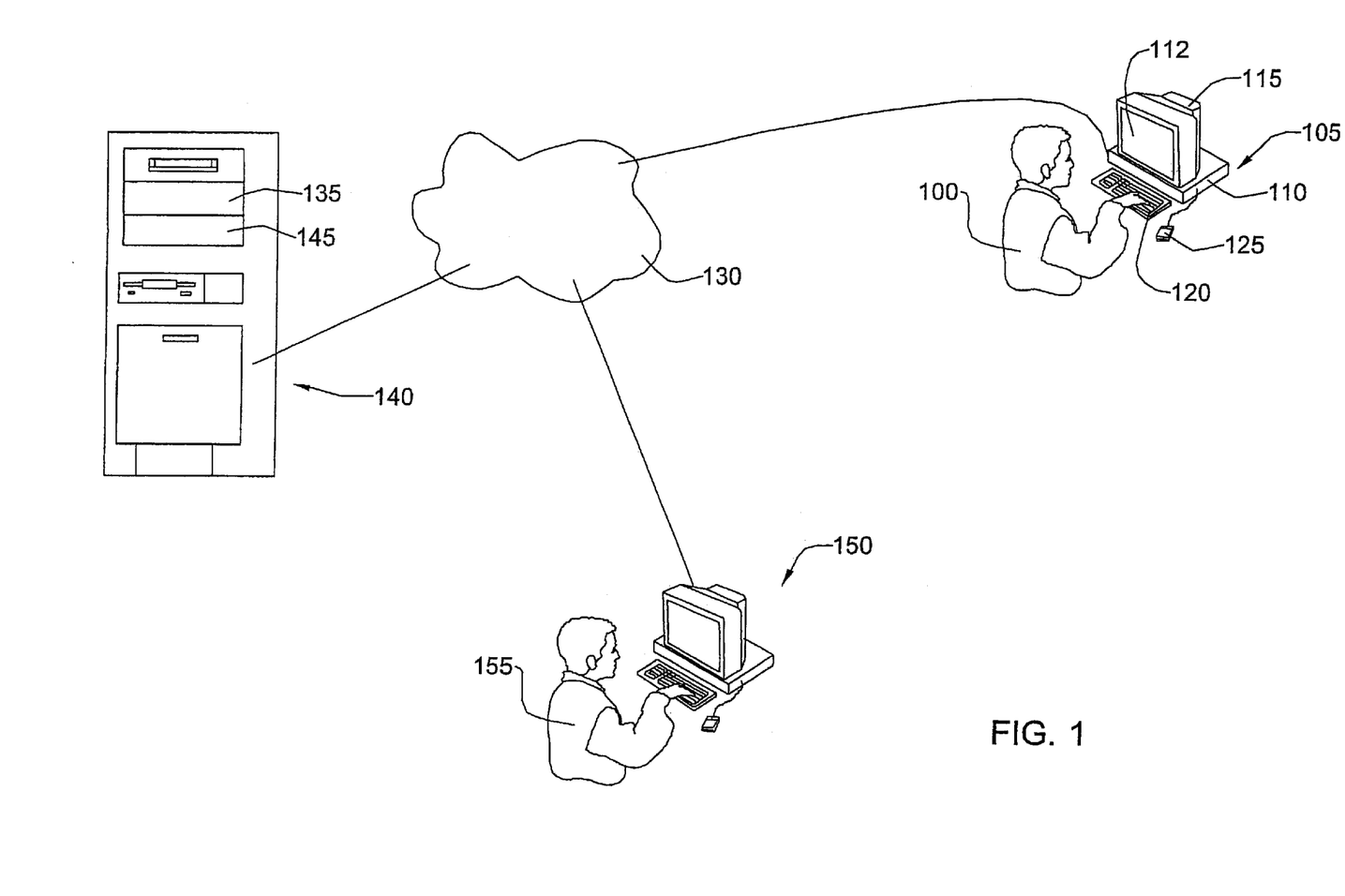
FIG. 1 is a system for detecting eye disease in accordance with one embodiment of the invention.

FIG. 1 shows a system for carrying out the invention according to one embodiment of the invention. A subject 100 performs an eye test using a computer terminal 105. The computer 105 comprises a computer 110, a monitor 115 having a screen 112 and one or more computer input devices such as a keyboard 120 or a computer mouse 125. The computer 105 communicates over a communication network indicated by the cloud 130. The network 130 may be, for example, the Internet, a local area network (LAN) or an Intranet.

A processor 135 in a network server 140 stores data relating to execution of an eye test to be performed by the subject 100 to be described in detail below. The eye test is communicated from the server 140 to the subject's computer 105 over the network 130. The subject 100 inputs responses to the eye test using one or more of the computer input devices such as the keyboard 120 or the mouse 125. The subject's responses are communicated over the network 130 to the processor 135, and stored in the memory 145. The processor is configured to analyze the subject's response, to make a diagnosis of the subjects conditions and to recommend future follow-up or recommend prompt examination, all in real time, for the subject. The diagnosis and recommendation are communicated over the network 130 to the subject's terminal 105 and/or to a terminal 150 of a health care provider 155. The processor 135 is also configured to store in the memory 145 dates on which the subject is to perform an eye test executed by the processor 135. If, for example, the subject 100 has been instructed by the health and provider 155 to perform the test once per week, the processor 135 may send a message over the communication network 130 when 10 days have elapsed since the last time he took the test, informing the subject of his failure to take the test as instructed. A similar message may be sent to the health care provider 155. A responsible individual may be designated, in such a case, to contact the subject 100, for example, by telephone to clarity why the subject 100 has not performed the test as instructed and to impress upon the subject the importance of performing the test as indicated.

Figure 2A:
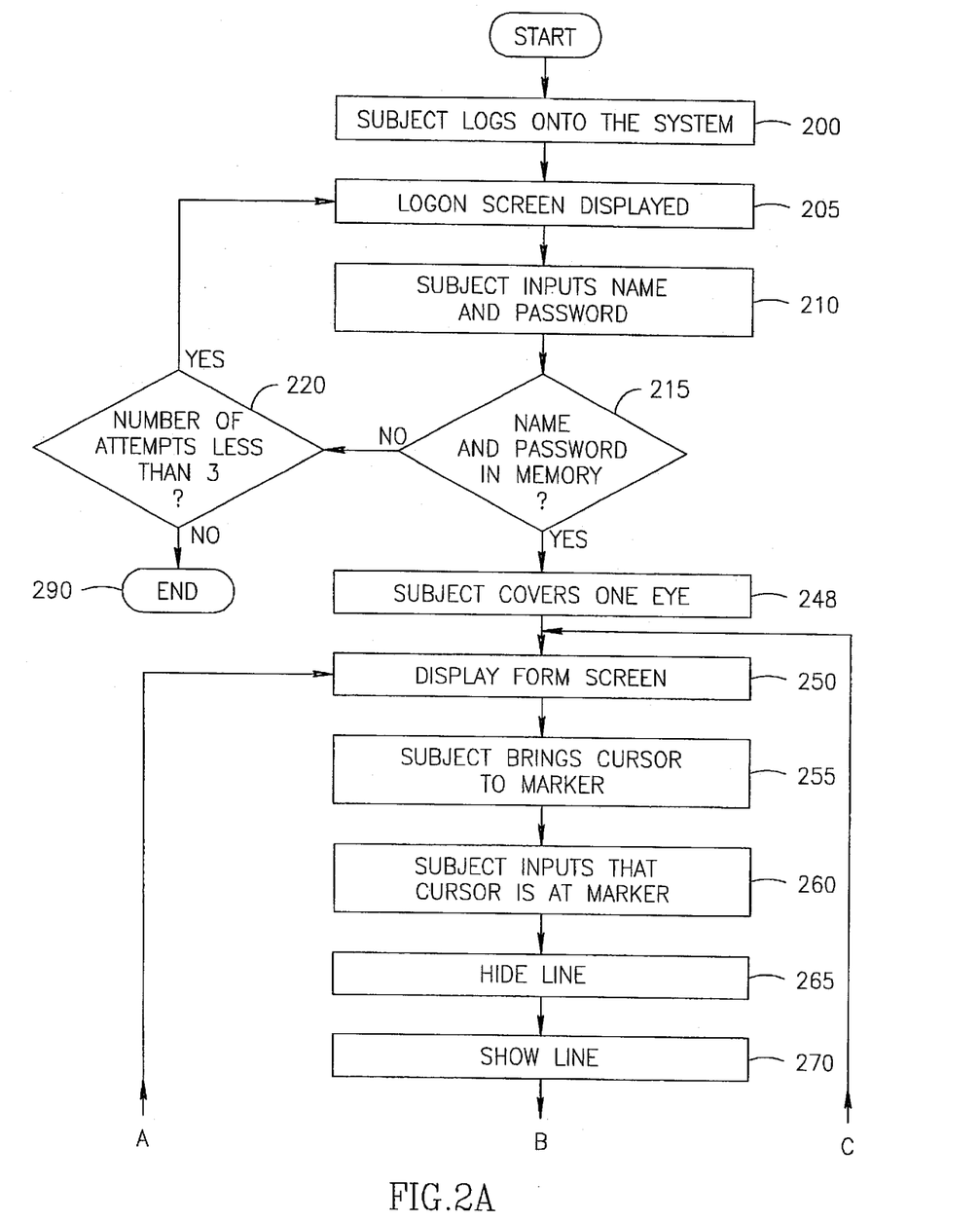
FIGS. 2A–2B are flow chart diagrams for a process of executing an eye test in accordance with one embodiment of the invention.
Figure 2B:
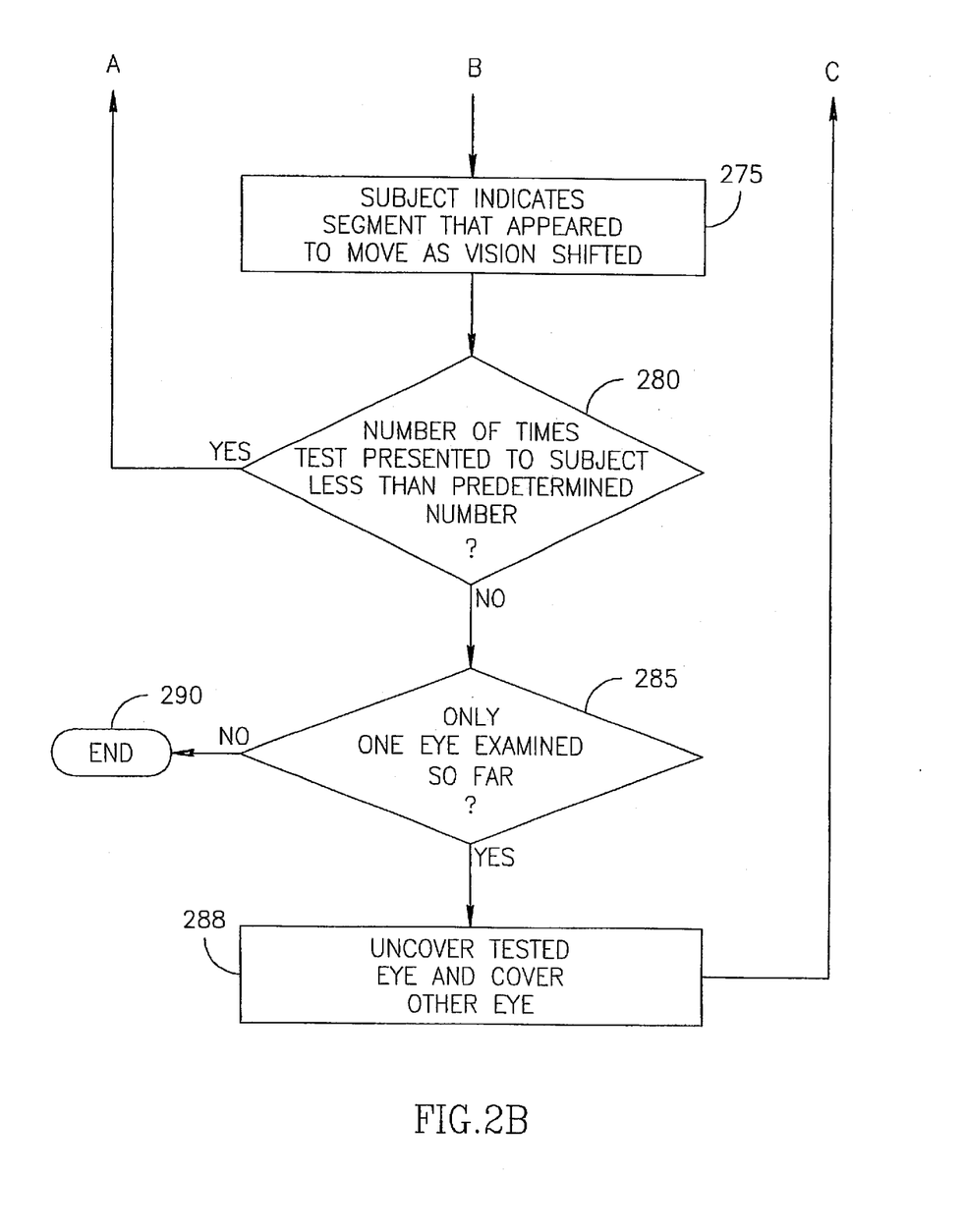
Figure 3:
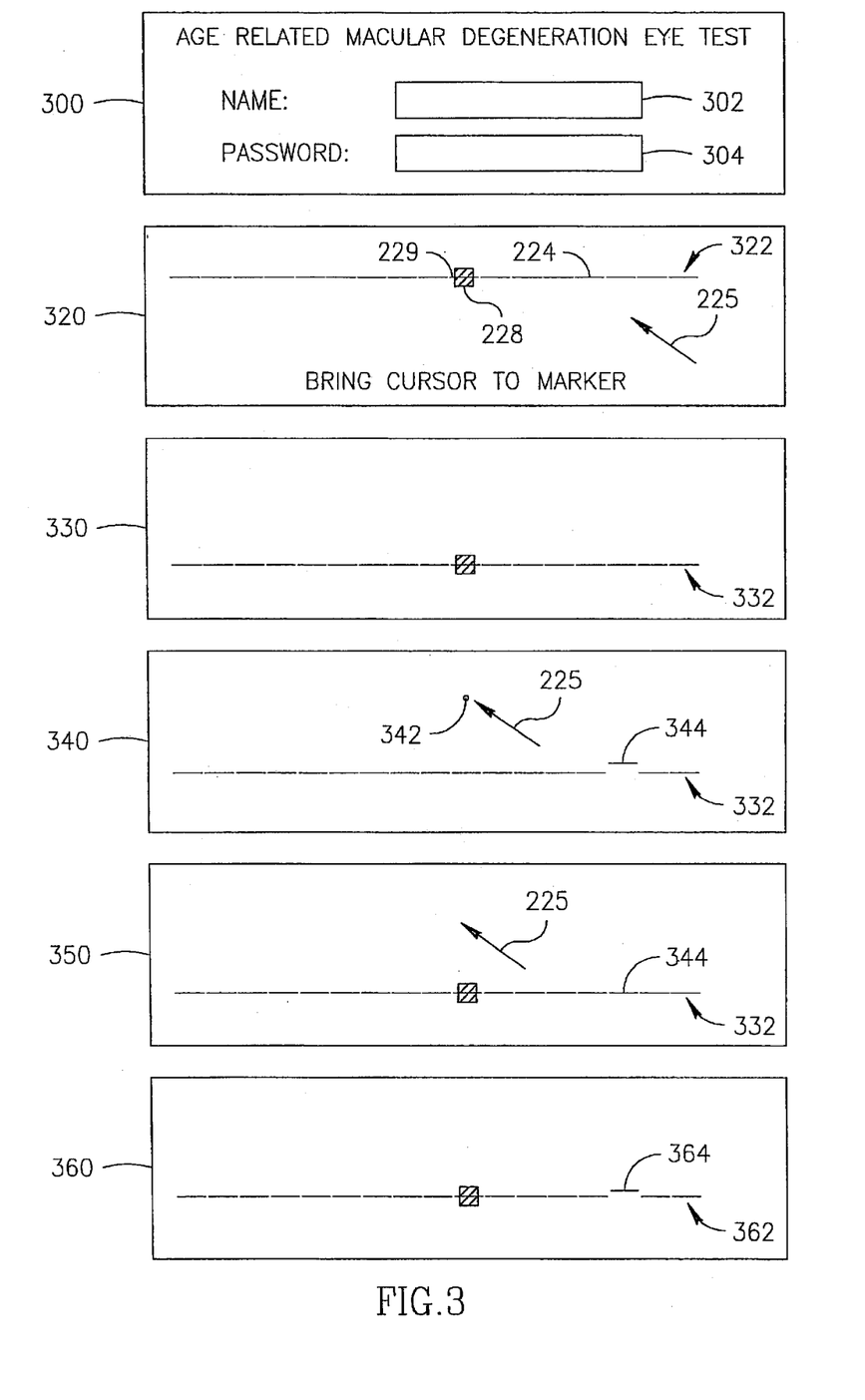
FIG. 3 are exemplary screens displayed on a computer monitor while carrying out the process of FIG. 2.

FIGS. 2A and 2B show a flow chart diagram for a process of executing an eye test over a system such as the one shown in FIG. 1, in accordance with the invention and FIG. 3 shows the appearance of the screen 112 of the subject's monitor 115 at various steps of the eye test.

In step 200, the subject 100 logs onto the processor 135. The processor 135 causes log-on screen 300 to be displayed on the subject's monitor 115 (step 205). The log-on screen 300 screen prompts the subject to input his name into a field 302 and a previously assigned password for accessing the processor 135 into a field 304. In step 210 the subject inputs his name and password using computer input devices such as the keyboard 120 or the mouse 125. The processor 135 then checks whether the inputted name and password are stored in the memory 145 (step 215). If no, processor determines whether the number of attempts the subject has made to input a name and password is less than a predetermined number such as 3 (step 220). If yes, the process returns to step 205. If no, the process terminates.

If at step 215 the processor determines that the name and password are in the memory 145, the process continues in step 248 by the subject covering an eye, so that the test is performed using one eye only. In step 250 a form screen 320 is displayed in which a pattern such as line 322 is displayed. This is by way of example only, and any pattern may be used within the scope of the invention. The pattern may consist of a single component, or consist of several components which may or may not be all identical. Thus, the pattern may consist of several lines, one or more circles, lines and circles together, etc. The screen of the monitor 115 may form a visually noisy background to a displayed pattern. The line 322 may be composed of several short segments, for example, the segment 224. Alternatively, the line may be continuous (not shown). The length of the line is preferably 1–20° in length, and may be horizontal as the line 322. Gaps between the segments are preferably between 0 to about 120 minutes arc. If the pattern consists of two or more parallel lines, the spacing between the lines is preferably from about 10 to about 600 minutes arc. The line may be vertical or slanted (not shown). A marker 228 is adjacent to one of the segments, for example the segment 229.

The subject is instructed to bring a cursor 225 appearing on the screen to the marker 228. In order to aid the subject, the cursor is restricted in its position to a line parallel to the line 322 so that the cursor always points to one of the segments. The subject performs this in step 255 using a computer device such as the keyboard 120, or more preferably the mouse 125. The marker 228 is sized so that it is large enough to see but small enough so that bringing the cursor 225 to the marker 228 is a demanding task for the subject. This causes the subject to fixate his vision on the marker. Upon bringing the cursor to the segment 229, the subject may click on his mouse 125 or depress a predetermined key on the keyboard 120 (step 260).

When the subject inputs that the cursor is positioned at the marker 228, indicating that his vision is fixated on the segment 229, the line 322 is made to disappear from the screen 320 (step 265). After a predetermined time interval (for example 0 to 200 milliseconds), a second pattern 332 is made to appear at a different location as shown in screen 330 (step 270) so as to allow the subject to form a perceived image of the second pattern 332. In this example, the pattern 332 is a line identical to the line 322 but appearing in a different location on the screen 112. The line 332 may, for example, be parallel to the line 322. Since the subject's vision had been fixated on the segment 229, the line 332 will appear in the periphery of the subject's field of vision. Any disturbance in his vision due to a retinal lesion such as AMD is apparent to the subject as a difference between the perceived image of the second pattern and a pre-defined pattern, which in this example is provided by the first pattern. For example, when the subject's vision is fixated at the location where the segment 229 had previously appeared (the point 342 in screen 340), a segment 344 of the line 332 may appear to be out of line with other segments in the line 332. Screen 340 shows a possible appearance of the screen 330 to an individual having a retinal lesion. In screen 340, the segment 344 is out of line with other segments in the line 332. This is by way of example only, and other differences between the perceived image and the pre-defined pattern may occur, such as a segment appearing blurred to the subject in the second pattern. As the subject subsequently shifts his vision to the line 332, the segment 344 appears to move into alignment with other segments in the line 332 as shown in screen 350.

The subject, in step 275, indicates which, if any, of the segments in the line 332 appeared different than corresponding segments in a predefined pattern. This may be done by the subject bringing the cursor 225 to the segment that appeared to move (the segment 344 in this example). This implicates the region in the subject's retina corresponding to the direction of the segment 344 as having a retinal lesion.

In step 280 it is determined whether the number of lines 322 presented to the subject is less than a predetermined number, such as 40. If yes the process returns to step 250 with a new line 322 being presented to the subject. Steps 250 to 280 are repeated several times, for example 40 times each time presenting the line 332 in a different location of the screen until the region of the subject's macular visual field has been completely mapped.

If it is determined in step 280 that the number of lines presented to the subject has reached the predetermined number, it is determined whether only one eye has been examined so far (step 285). If yes, the subject is instructed to uncover his eye and to cover the other eye (288). The process then returns to step 250 with the subject testing his other eye. If no, the process terminates at step 290.

The position of the line 322 presented to the subject is varied each time in order to completely cover the fovea so as to detect any regions affected with AMD. Areas are preferably mapped more than once, and at a higher resolution (several successive lines 322 relatively close to one another).

As shown in screen 360, instead of the line 332 having only aligned segments, a line 362 actually having a displaced segment 364 may be presented to the subject, for example, for a duration up to about 300 msec. This is done to ascertain that the subject is aware of the visual associated with AMD, and that his responses reliably reflect the perceived appearance of lines presented to him.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

What is claimed is:

1. A method for detecting eye disease in an individual, comprising steps of:
   (a) displaying to the individual a first pattern at a first location on a surface, the first pattern comprising at least one point;
   (b) fixating the individual's vision on a point in the first pattern;
   (c) hiding at least a portion of the first pattern;
   (d) displaying a second pattern to the individual at a second location on the surface so as to allow the individual to form a perceived image of the second pattern;
   (e) obtaining a comparison of the perceived image and a predefined pattern;
   (f) repeating steps (a) to (e) a number of times; and
   (g) determining whether the individual has an eye disease based on the comparisons.

2. The method according to claim 1 wherein the second pattern and the predefined pattern are substantially identical, an eye disease being detected when the perceived image and the predefined pattern are not identical.

3. The method according to claim 1 wherein the second pattern and the predefined pattern are not identical.

4. The method according to claim 3 wherein the second pattern is similar to an image of the predefined pattern perceived by an individual with eye disease.

5. The method according to claim 3 wherein the predefined pattern comprises a plurality of components and the second pattern is obtained by a modification of the predefined pattern, the modification being selected from the group consisting of:
   displacing at least one component of the predefined pattern,
   removing at least one component of the predefined pattern,
   blurring at least one component of the predefined pattern, and
   changing an optical property of at least one component of the predefined pattern.

6. The method according to claim 1 wherein the predefined pattern or the second pattern comprises one or more lines.

7. The method according to claim 6, wherein one or more of said lines is a broken line comprising a plurality of segments.

8. The method according to claim 1 wherein the predefined pattern comprises a plurality of identical components.

9. The method according to claim 1 wherein the predefined pattern comprises a plurality of components at least two of which are not identical.

10. The method according to claim 1 wherein the second pattern is obtained by rotation and/or translation of the predefined pattern.

11. The method according to claim 7 wherein the gaps between said segments are between 0 and 120 minutes arc in length, and each segment of said plurality of segments has a height and a width between 1 and 120 minutes arc.

12. The method according to claim 6 wherein the predefined pattern or the second pattern comprises two or more parallel lines.

13. The method according to claim 12 wherein the spacing between at least one pair of adjacent parallel lines of said two or more parallel lines is from about 10 to about 600 minutes arc.

14. The method according to claim 1 wherein the step of obtaining a comparison of the perceived image and the predefined pattern comprises the individual's indicating a difference between the predefined pattern and the perceived image.

15. The method according to claim 14 wherein the difference is selected from the group consisting of:
   a component of the predefined pattern that is displaced in the perceived image;
   at least one component of the predefined pattern that is missing in the perceived image;
   at least one component of the predefined pattern that is blurred in the perceived image; and
   at least one component of the predefined pattern having an altered optical property in the perceived image.

16. The method according to claim 1, wherein the surface is a monitor screen.

17. The method according to claim 16 wherein the pattern comprises at least one immobilized component that flashes on and off at least once.

18. The method according to claim 16 wherein the pattern comprises at least one moving component.

19. The method according to claim 16, wherein the step of fixating the individual's vision on a point on the screen comprises the individual's bringing a cursor to the point.

20. The method according to claim 19 wherein the second pattern appears on the screen upon the individual's clicking a mouse when the cursor is on the point.

21. The method according to claim 16 wherein the surface forms a visually noisy background to a displayed pattern.

22. The method according to claim 19 wherein the cursor is restricted to a path adjacent to the pattern.

23. The method according to claim 1, further comprising a step of producing an analysis of one or more comparisons so as to determine existence, extent, type, or location of an eye disease in the individual.

24. The method according to claim 16 wherein one or more comparisons are transmitted over a communication network to a processor and stored in a memory.

25. The method according to claim 24 wherein the communication network is a computer network such as local area network, a wide area network, the Internet, an intranet, a LAN, a WAN or a PAN.

26. The method according to claim 24 wherein one or more comparisons are transmitted over the communication network in real time.

27. The method according to claim 24, further comprising a step of transmitting over the communication network times at which the method is performed by the individual and storing the times in a memory.

28. The method according to claim 27 further comprising a step of sending a reminder to the individual to perform the test if the individual fails to perform the test as instructed by a health care provider.

29. The method according to claim 27, further comprising a step of transmitting over the communication network in real time to a health care provider of results of an analysis of the comparisons.

30. The method according to claim 2, wherein the first and second patterns are displayed on a monitor screen, the predefined pattern is a broken line comprising a plurality of segments, and the step of obtaining a comparison of the perceived image and the predefined pattern comprises bringing a cursor to a segment in the second pattern perceived by the individual to be misaligned relative to other segments, blurred relative to other segments, or absent.

31. The method according to claim 3, wherein the first and second patterns are displayed on a monitor screen, the predefined pattern is a broken line comprising a plurality of segments, the second pattern is obtained from the predefined pattern by misaligning at least one segment relative to other segments of the broken line, blurring of at least one segment relative to other segments of the broken line, altering an optical property of at least one segment of the broken line, or removing of at least one segment of the broken line, and the step of obtaining a comparison of the perceived image and the predefined pattern comprises indicating a region of said screen in the vicinity of a segment in said second pattern perceived by the individual to be misaligned relative to other segments of said second pattern, to be blurred relative to other segments of said second pattern, to have optical properties different than the optical properties of other segments of said second pattern, or to be absent in said second pattern, respectively.

32. The method according to claim 1 wherein the eye disease is a retinal lesion.

33. The method according to claim 32 wherein the retinal lesion is AMD or diabetes related.

34. The method according to claim 1 wherein steps (a) to (e) are repeated 40 to 80 times.

35. A system for detecting eye disease in an individual, comprising:
   a surface configured to display a first pattern to the individual, said first pattern comprising at least one point;
   a device for fixating the individual's vision on a point in a pattern displayed on said surface and for hiding at least a portion of said pattern after the individual'vision has been fixated on the point;
   a device for selecting a portion of a pattern displayed on said surface; and
   a processor configured to carry out the steps of,
      displaying to the individual a first pattern at a first location on a surface, the first pattern comprising at least one point,
      determining when the individual's vision is fixated on a point in said first pattern,
      hiding at least a portion of the first pattern upon the individual fixating his vision on a point in the first pattern,
      displaying a second pattern to the individual at a second location on the surface so as to allow the individual to form a perceived image, and
      obtaining a comparison of said perceived image and a predefined pattern.

36. The system according to claim 35 wherein said surface is part of a display device operatively coupled to said device for fixating.

37. The system according to claim 35 wherein the device for selecting a portion of a pattern comprises an input device operatively coupled to said device for fixating the individual's vision on a point of the surface.

38. The system according to claim 35 wherein the device for selecting a portion of a pattern comprises a pointing device for operatively moving a cursor on said screen.

39. A program storage device readable by machine, tangibly embodying a program of instructions executable by the machine to perform method steps for detecting eye disease in an individual, comprising the steps of:
   displaying to the individual a first pattern at a first location on a surface, the first pattern comprising at least one point;
   determining when the individual's vision is fixated on a point near or in the pattern;
   hiding at least a portion of the first pattern upon the individual fixating his vision on a point in the first pattern;
   displaying a second pattern to the individual at a second location on the surface so as to allow the individual to form a perceived image; and
   obtaining a comparison of the perceived image and a predefined pattern.

40. A computer program product comprising a computer useable medium having computer readable program code embodied therein for detecting eye disease in an individual, the computer program product comprising:
   computer readable program code for causing a computer to display a first pattern to the individual at a first location on a surface;
   computer readable program code for causing the computer to determine when the individual's vision is fixated on a point on said surface and for hiding at least a portion of the first pattern when the individual's vision is fixated on said point;
   computer readable program code for causing the computer to display a second pattern to the individual at a second location on said surface to allow the individual to form a perceived image of said second pattern; and,
   computer readable program code for causing the computer to obtain a comparison of said perceived image and a predefined pattern.

41. A system for detecting eye disease in an individual, the system comprising:
   means for displaying patterns to the individual;
   means for fixating the individual's vision on a point in a pattern displayed on said means for displaying and for biding at least a portion of said pattern after the individual's vision has been fixated on said point;
   means for selecting a portion of a pattern displayed on said means for displaying;

processing means operatively coupled to said means for displaying, and said means for selecting and configured to perform the steps of, displaying to the individual a first pattern at a first location on said means for displaying, the first pattern comprising at least one point, determining when the individual's vision is fixated on a point in said first pattern, hiding at least a portion of said first pattern upon the individual fixating his vision on said point of said first pattern, displaying a second pattern to the individual at a second location on said means for displaying to allow the individual to form a perceived image of said second pattern, and obtaining a comparison of said perceived image and a predefined pattern.

42. The system according to claim 37 wherein said input device is selected from a computer mouse, a keyboard, a joystick, and a touch screen.

* * * * *